United States Patent [19]

Sixsmith

[11] Patent Number: 5,322,694
[45] Date of Patent: Jun. 21, 1994

[54] PHARMACEUTICAL LOZENGES

[75] Inventor: David G. Sixsmith, Farnham, England

[73] Assignee: Merrell Dow Pharmaceuticals Inc., Cincinnati, Ohio

[21] Appl. No.: 847,856

[22] Filed: Mar. 9, 1992

Related U.S. Application Data

[63] Continuation of Ser. No. 625,724, Dec. 10, 1990, abandoned.

[30] Foreign Application Priority Data

Dec. 13, 1989 [GB] United Kingdom ............... 8928196

[51] Int. Cl.$^5$ ................................................ A61K 9/20
[52] U.S. Cl. ...................... 424/440; 424/439; 424/441; 424/464; 424/465; 424/470; 424/488; 514/960
[58] Field of Search ............... 424/440, 439, 441, 464, 424/465, 470, 488; 514/960

[56] References Cited

U.S. PATENT DOCUMENTS 4,624,849  11/1986  Toogood ..................... 424/78.01

FOREIGN PATENT DOCUMENTS 0100157  7/1983  European Pat. Off. .
0409279  7/1990  European Pat. Off. .
2009597  6/1978  United Kingdom .

OTHER PUBLICATIONS

Gennaro. (1985). Remington's Pharmaceutical Sciences. Mack Publishing Co., Pa.
Oakenfull, D. et al. (1986). Food Hydrocolloids vol. 1, No. 2, pp. 163-176.
Acta Pharmaceutica Fennica, vol. 87, No. 2, 1978, pp. 61-73.

*Primary Examiner*—Thurman K. Page
*Assistant Examiner*—Raj Bawa
*Attorney, Agent, or Firm*—Michael J. Sayles

[57] ABSTRACT

The present invention is directed to gelatin treated polyhydric alcohol compositions, their preparation, and to pharmaceutical lozenges prepared therefrom. The pre-granulation of a polyhydric alcohol with an aqueous gelatin solution prior to compression, produces lozenges having a delayed rate of dissolution.

6 Claims, No Drawings

PHARMACEUTICAL LOZENGES

This is a continuation of application Ser. No. 07/625,724, filed Dec. 10, 1990, now abandoned.

The present invention is directed to polyhydric alcohol based lozenges having a delayed rate of dissolution. Another aspect of the invention is directed to an inert polyhydric alcohol based carrier which will produce such lozenges. Another aspect of the invention is directed to a method for producing such a lozenge.

Lozenges or troches are pharmaceutical dosage forms which are used to treat disease states affecting the tissues contained within the oral cavity and throat. A typical lozenge or troche is composed predominantly of an inert vehicle, carrier, or diluent. A medicinal agent is interspersed within this carrier. The lozenge will slowly dissolve when placed in the oral cavity thereby releasing the medicinal agent so that it may come in contact with the tissues of the mouth and throat. These dosage forms are typically used to treat conditions such as throat infections, dental plaque, halotosis, etc.

Typically the carrier material is a sugar such as sucrose, dextrose, etc. Recently consumers have become concerned about the excessive levels of sugar contained within their diets. This concern has caused a demand for sugar-free products, including sugar-free medications. Pharmaceutical manufacturers have attempted to find alternative carrier bases in order to provide sugar-free lozenges. One such alternative carrier is a polyhydric alcohol such as xylitol. Polyhydric alcohols are considered as a viable alternative because they provide a sweet taste will mask the bitter taste of many medicinal agents. Lozenges made from polyhydric alcohols do suffer from one serious disadvantage. They dissolve very rapidly when placed in the oral cavity. For example a lozenge made from a xylitol based carrier will dissolve completely within approximately 3 minutes of administration. Other polyhydric alcohols such as sorbitol or mannitol will also dissolve within 3 minutes of administration. Thus the medicinal agents are released so rapidly that a large percentage of the dose is washed into the patients alimentary canal rather than having an opportunity to come in contact with the tissues of the oral cavity which are under treatment. Thus it would be a valuable contribution to the art to produce polyhydric alcohol based lozenges having slower rates of dissolution within the oral cavity.

The present invention is directed to a polyhydric alcohol based carrier which will produce lozenges having decreased rates of dissolution relative to the polyhydric alcohol lozenges currently available. It has been discovered that if the polyhydric alcohol based carrier is granulated with a gelatin solution, any lozenges produced from this carrier will have a delayed rate of dissolution within the oral cavity. It has also been discovered that the dissolution rates of these lozenges can be further delayed if a hydrophobic lubricant is incorporated into the carrier at levels of at least 2 w/w%.

As used in this application:

a) the term "polyhydric alcohol" should be construed as describing the following substances: xylitol, mannitol, sorbitol, maltitol, isomaltitol, maltotriitol, lactitol, α-1-glucopyranasido-1,6-mannitol, and β-linked-glucopyranasido-sorbitol.

b) the term "polyhydric alcohol carrier" should be construed as describing a diluent, carrier, or vehicle which is suitable for compounding into a lozenge, in which the bulking agent is a polyhydric alcohol. This "polyhydric alcohol carrier" may also contain excipients commonly used in the preparation of sugar-free lozenges. Examples of such excipients include an additional sugar-free diluent such as mannitol or sorbitol, antiadherants such as colloidal silica, lubricants which are known in the art, and flavoring agents known in the art.

c) the terms "gelatin treated polyhydric alcohol based carrier" or "gelatin treated polyhydric alcohol" should be construed as describing a composition containing a polyhydric alcohol and optionally containing other pharmaceutical excipients which has been granulated with a gelatin solution, and optionally dried and milled to a particle size suitable for incorporation into a lozenge;

d) the terms "lozenge or troche" are used interchangeably in this application and refer to a medicated tablet or disk which will dissolve in the oral cavity thereby releasing its medication for the treatment of tissues within this cavity;

e) the term "lozenge" should be construed as encompassing only those lozenges which are manufactured by compression methods and;

f) the terms "carrier, diluent, and vehicle," are used interchangeably and refer to an inert excipient which serves primarily as the bulking agent in the lozenge.

Xylitol is one of the polyhydric alcohols which is suitable for use in the present invention. It is also the preferred polyhydric alcohol. It is known in the pharmaceutical arts as a sweetener. Its chemical name is 1,2,3,4,5-pentanpentol. It also has been referred to as xylit, xilitol, xylitolo, klinit and pentapentol. This substance is available from numerous commercial sources, such as, for example, Hoffman La Roche, Esai Co. Ltd., Finnsugar, and Roquette. Methods of manufacturing this substance are taught in the Handbook of Pharmaceutical Excipients, jointly published by the American Pharmaceutical Association and The Royal Pharmaceutical Society of Great Britain (1986).

Mannitol is known as an excipient. This substance's chemical name is 1,2,3,4,5,6-hexanehexol. It has been referred to as manite, manna sugar, and as manita. This substance is also available from numerous commercial sources and its method of manufacture is taught in the Handbook of Pharmaceutical Excipients, id.

Sorbitol is also a well known pharmaceutical excipient. It's chemical name is 1,2,3,4,5,6,-hexanehexol. It has also been referred to as d-glucitol, d-sorbitol, sorbite, and sorbol. This substance is also available from numerous commercial sources and its method of manufacture is taught in the Handbook of Pharmaceutical Excipients, id.

The other polyhydric alcohols which may be utilized in the present invention are maltitol, isomaltitol, maltotritol, lactitol, α-1-glucopyranasido-1,6-mannitol, and β-linked-glucopyranasido-sorbitol. These compounds are also well known in the art as sugar-free substitutes. For example, see *CHEMICAL TECHNOLOGY REVIEW*, No. 30, Tablet Manufacture, Noyes Data Corporation, (1974) or *SILESIA CONFISERIE MANUAL NO. 3*. They are available from numerous commercial suppliers, such as, for example, Aldrich, Finnsugar, or Roquette.

As noted above, one aspect of the present invention is directed to a method for producing a gelatin treated polyhydric alcohol based carrier, which after proper compression will produce lozenges having delayed rates of dissolution within the oral cavity. This result is by granulating the polyhydric alcohol with a gelatin solution. This treatment should be carried out prior to the time at which the carrier is compounded into a dosage form.

This granulation is typically carried out in the following manner. The powdered polyhydric alcohol is optionally dry blended with a dispersing agent such as microcrystalline cellulose. The function of the dispersing agent is to improve the distribution of the gelatin through the powdered polyhydric alcohol. Other suitable dispersing agents include starches, untreated celluloses and modified celluloses. The quantity of dispersing agent that is utilized can vary widely. However, the dispersing agent is generally present in this blend in the quantity of from about 1-20 w/w% and more preferably from about 2 to 10 w/w% and most preferably about 4.5-5.5 w/w%.

The next step in the process is to granulate the blend of polyhydric alcohol and dispersing agent with the gelatin solution. This is accomplished by contacting the blended polyhydric alcohol with the gelatin solution in a high speed granulator for a period of time ranging from about 2 to 10 minutes. The quantity of gelatin that is utilized can vary widely. However, the quantity of gelatin utilized should be such that when the resulting granule is dried to a moisture content below 1.0 w/w%, the gelatin will be present within a range of from about 0.1 to about 5 w/w% and more preferably about 1.4 w/w%. For example, if a 25 w/w% solution of gelatin is utilized, then from about 50 to about 55 millilitires of this solution will be mixed with about 1000 grams of the blend of polyhydric alcohol and dispersing agent.

The particular gelatin which is utilized to granulate the polyhydric alcohol is not critical. Any commercially available gelatin which meets the specifications of either the United States Pharmacopoeia or the British Pharmacopoeia is suitable for use in the instant invention. Such grades of gelatin are available from numerous commercial suppliers including Rousselot.

The resulting gelatin treated polyhydric alcohol granules are then dried in order to reduce their water content to a level below 1 w/w% and more preferably below 0.7 w/w%. If excessive levels of moisture remain within the granule then it will be difficult to compress the gelatin treated polyhydric alcohol in a satisfactory manner. The granules may be dried using techniques known in the art. One suitable method for drying the granules is to tray dry them in a hot air oven.

After the granules have been dried, they are typically milled in order to decrease the particle size of the individual granules. If the particle size of the granules is too large, the lozenges produced from these granules will tend to have a gritty feel in the patients mouth. It is preferred for the polyhydric alcohol granules to have a mean particulate size in the range of from about 140 to 200 microns. The granules can be milled using techniques well known in the art such as passing the granules through a meshed screen. A 1.25mm screen will produce granules suitable for incorporation into the dosage forms of the present invention. A screen capable of producing smaller particles may be used if desired though. The milled granules are typically dry blended with from 1 to 5 w/w% of an anticaking agent such as colloidal silicon dioxide prior to their utilization in the compounding of any lozenge.

The resulting gelatin treated polyhydric alcohol based carrier may be utilized in the compounding of lozenges and troches. Methods for producing lozenges and troches are well known in the art. Typically a medicinal agent, and excipients such as anti-adherants, flavoring agents, lubricants, etc. are dry blended with the carrier and the mixture is then compressed in order to produce a lozenge or troche. More detailed descriptions for producing troches and lozenges are taught in Pharmaceutical Dosage Forms Vol. 1. The resulting lozenges will take at least 6 minutes to completely dissolve within the oral cavity.

As noted above, the dissolution rate of the lozenge can be further delayed if a hydrophobic lubricant is present in the lozenge at levels of at least 2 w/w% and more preferably at a level between 2-10 w/w%, and most preferably about 3 w/w%. Hydrophobic lubricants suitable for delaying this dissolution rate include magnesium stearate, calcium stearate, zinc stearate, stearic acid, sterotex, talc, emulsifying wax, microcrystalline wax, white wax, or yellow wax. All of these lubricants are well known in the art and are available from numerous commercial sources.

When a lubricant is being utilized to further delay the dissolution rate of the lozenge, the lubricant should be incorporated into the carrier base after the other excipients and medicinal agent or agents have been incorporated into the base. This is typically accomplished by dry blending the mixture of carrier, excipients and medicinal agent with one of the lubricants listed above. The dry blending should be carried out for a period of time ranging from about 1 to 30 minutes.

Once the lubricant is incorporated into the mixture of carrier, excipients and medicinal agent, the resulting composition can be compressed into a lozenge using the techniques described above. The resulting lozenges will take at least 8 minutes to completely dissolve within the oral cavity.

The gelatin treated polyhydric alcohol based carrier produced by this process will typically have the following composition:

TABLE I

| COMPONENT | AMOUNT[1] (w/w %) |
|---|---|
| POLYHYDRIC ALCOHOL | 60-99 |
| DISPERSING AGENT | 0-20 |
| GELATIN | 0.1-5 |
| ANTI-CAKING AGENT | 0-5 |
| LUBRICANT | 0-10 |

[1]When dried to a moisture content of approximately 1% w/w.

Any of the medications which are typically incorporated into lozenges may be utilized in the present invention An individual medication can be incorporated into the lozenge or multiple medications can be incorporated into the lozenge. For example, antimicrobial agents are typically incorporated into lozenges in order to treat throat infections and plaque. Antimicrobial agents suitable for use in the present invention include cetylpyridinum chloride, benzalkonium chloride, domiphen bromide, chlorhexidine, clioquinol, or tyrothricin. The quantity of antimicrobial agent that will be incorporated into the lozenge will vary depending upon the specific agent utilized. Typically from about 1 to about 20 mg of antimicrobial agent will be utilized per lozenge.

Local anesthetics are also incorporated into lozenges in order to treat sore throats. Local anesthetics which may be incorporated into the lozenges of the instant invention include benzocaine, lidocaine, or hexylresorcinol. The quantity of anesthetic required can vary widely but will typically range from about 1 to 20 mg per lozenge.

Anti-fungal agents are also typically incorporated into lozenges in order to treat fungal infections. Suitable anti-fungal agents for use in the present invention include nystatin or clotrimizole. The quantity of anti-fungal agent required will also vary widely but are well known to those skilled in the art.

Medications to control coughs can also be incorporated into these lozenges. Such medications include dextromorphan or codeine. Typically each lozenge will contain from about 5 to about 60 milligrams of cough suppressant.

Breath fresheners are also routinely incorporated into lozenges in order to minimize halotosis. Other medications which may be administered by the lozenges of the instant invention include: ascorbic acid, eutectics such as menthol and phenol, phenol and phenolate, or euclyptus oil and menthol. The quantity of these agents can vary widely but are well known to those skilled in the art.

The pharmaceutical composition of the present invention demonstrates acceptable in vivo dissolution characteristics which indicate that the composition provides effective levels of therapeutically active ingredients at the oral pharangeal mucosal surfaces over a relatively prolonged period.

The dosage range of these lozenges can vary widely depending upon the amount and type of active ingredient contained within the dosage form, the patient and severity of symptoms etc. Typically the dose will be one lozenge administered from 4 to 8 times daily.

As used in this application, the term "patients" refers to a warm blooded mammal such as, for example, rabbits, mice, rats, guinea pigs, chimpanzees, humans etc.

The following examples are being provided in order to further illustrate the invention but should not be construed as limiting the scope in any manner.

EXAMPLE I

The following table illustrates the composition of the currently preferred pharmaceutical composition of the present invention:

TABLE II

|  | Mg/Lozenge |
|---|---|
| Xylitol milled | 691.1 |
| Microcrystalline Cellulose (Avicel PH101) | 37.4 |
| Gelatin | 10.0 |
| Cetylpyridinium Chloride Monohydrate | 2.5 |
| Citric Acid Monohydrate | 13.0 |
| Silesia Flavour | 6.0 |
| Silicon Dioxide Amorphous (Aerosil 300) | 16.0 |
| Magnesium Stearate | 24.0 |
|  | 800.00 |

METHOD OF MANUFACTURE

The lozenge was manufactured in the following manner:

In a high intensity mixer, 172,755 kg of xylitol (milled), and 9.35 kg of microcrystalline cellulose were combined and mixed thoroughly. A granulation solution (consisting of 2.5 kg gelatin dissolved in 7.5 kg purified water at 50° C. was prepared and slowly added to the powder blend with mixing. Mixing continued until granules were formed. The granulation was dried to a moisture content of approximately 1.5% (loss on drying method). The granulation was then milled using a Fitzmill with a 2mm screen before further drying to below a moisture content of 1% (loss on drying method). The dried granule was milled using a Fitzmill equipped with a 1.2 mm screen.

To the sized granule was added after screening and preblending 8.0 kg silicon dioxide (amorphous), 3.0 kg silesia flavor and 1.25 kg cetylpridinium chloride monohyrate. The resultant mixture was blended in a V-blender until a uniform mixture was achieved.

To this mixture was added 12.0 kg magnesium stearate and the resulting mixture blended until a suitably mixed lubricated granule was achieved.

The granulation was fed to a suitable tablet press and lozenges with an average weight of approximately 800 mg were compressed.

Approximately 500,000 lozenges were compressed. The average lozenge weight was 802 mg, thickness 4.5–4.6 mm, diametral crushing strength 8–9.5 Kp, friability 0.7% and disintegration time GT 8 minutes.

What is claimed is:

1. A granulated, gelatin treated polyhydric alcohol pharmaceutical composition consisting essentially of granules having from 60–99% w/w% of a polyhydric alcohol selected from the group consisting of xylitol, sorbitol, and mannitol, a therapeutically effective amount of a pharmaceutical, and from about 0.1 to about 5 w/w% of gelatin, optionally in combination with from 0–20 w/w% of a dispersing agent and form 0–5 w/w% of an anti-caking agent, and wherein the granules when dried are a particle size of about 140 to about 200 microns and a water content of 1 w/w%.

2. A carrier according to claim 1 which contains at least 2 w/w% of a lubricant.

3. A carrier according to claim 1 in which the polyhydric alcohol is xylitol.

4. A lozenge according to claim 2 wherein said polyhydric alcohol is xylitol.

5. A lozenge according to claim 2 containing at least 2 w/w% of a lubricant.

6. A method for producing a gelatin treated polyhydric alcohol based lozenge which consisting essentially of:

a) contacting a polyhydric alcohol selected from the group consisting of xylitol, sorbitol, and mannitol with a solution of gelatin to form granules having a polyhydric alcohol content of from 60–99 w/w% of polyhydric alcohol, a gelatin content of from about 0.1 to about 5 w/w% of gelatin, and optionally in combination with 0–20 w/w% of a dispersing agent and from 0–5 w/w % of an anti-caking agent;

b) drying said gelatin treated polyhydric alcohol granules to a water content of about 1 w/w%, and milling said dried granules to a particle size of from about 140 to about 200 microns, and;

c) blending said milled granules with pharmaceutical excipients and at least one pharmaceutically active ingredient and;

d) compressing the resulting mixture into a lozenge dosage form.

* * * * *